United States Patent [19]
Holmes-Farley et al.

[11] Patent Number: 6,129,910
[45] Date of Patent: Oct. 10, 2000

[54] WATER-INSOLUBLE NONCROSSLINKED BILE ACID SEQUESTRANTS

[75] Inventors: Stephen Randall Holmes-Farley, Arlington; W. Harry Mandeville, III, Lynnfield, both of Mass.

[73] Assignee: GelTex Pharmaceuticals, Inc., Waltham, Mass.

[21] Appl. No.: 08/999,351

[22] Filed: Dec. 29, 1997

Related U.S. Application Data

[63] Continuation-in-part of application No. 08/659,264, Jun. 6, 1996, Pat. No. 5,900,475, which is a continuation-in-part of application No. 08/169,659, Jun. 6, 1995, Pat. No. 5,618, 530, which is a continuation-in-part of application No. 08/258,431, Jun. 10, 1994, abandoned, and a continuation-in-part of application No. 08/332,096, Oct. 31, 1994, abandoned, and a continuation-in-part of application No. 08/482, 969, Jun. 7, 1995, Pat. No. 5,703,188, which is a continuation-in-part of application No. 08/258,477, Jun. 10, 1998, Pat. No. 5,624,963, which is a continuation-in-part of application No. 08/071,564, Jun. 2, 1993, abandoned, and a continuation-in-part of application No. 08/779,779, Jan. 1, 1997, Pat. No. 5,919,832, which is a division of application No. 08/471,769, Jun. 6, 1995, Pat. No. 5,607,669, which is a continuation-in-part of application No. 08/258,431, Jun. 10, 1994, abandoned, and a continuation-in-part of application No. 08/461,298, Jun. 5, 1995, Pat. No. 5,693,675, and a continuation-in-part of application No. 08/910,692, Aug. 13, 1997, abandoned, which is a division of application No. 08/460,980, Jun. 5, 1995, Pat. No. 5,679,717, said application No. 08/461,298, Jun. 5, 1995, Pat. No. 5,693,675, said application No. 08/460,980, Jun. 5, 1995, Pat. No. 5,679, 717, is a continuation-in-part of application No. 08/258,431, Jun. 10, 1994, abandoned.

[51] Int. Cl.[7] .................................................. A61K 31/785
[52] U.S. Cl. ........................... 424/78.12; 424/78.27; 526/290; 528/392
[58] Field of Search .......................... 424/78.12, 78.27, 424/486, 497; 514/824; 526/290; 528/392

[56] References Cited

U.S. PATENT DOCUMENTS 2,874,132   2/1959   Riener .
3,288,770  11/1966   Butler ..................................... 260/88.3
3,308,020   3/1967   Wolf et al. ................................ 167/65

(List continued on next page.)

FOREIGN PATENT DOCUMENTS 0 081 291 A3   6/1983   European Pat. Off. .
0 162 388     11/1985   European Pat. Off. .
0 323 847 A1   7/1989   European Pat. Off. .

(List continued on next page.)

OTHER PUBLICATIONS

Heming, A.E. and Flanagan, Thomas L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

Butler, G.B. and Do, C.H., "Comblike Cyclopolymers of Alkyldiallylamines and Alkyldiallylmethylammonium Chlorides," in *Water–Soluble Polymers*, eds. Shalaby, McCormick & Butler, Chapter 9, pp. 151–158 ACS Symposium Series 467 (1991).

(List continued on next page.)

*Primary Examiner*—Thurman K. Page
*Assistant Examiner*—R. Bawa
*Attorney, Agent, or Firm*—Hamilton, Brook, Smith & Reynolds, P.C.

[57] ABSTRACT

The present invention relates to a method for sequestering bile acids in a patient and to particular polymers for use in the method. The method comprises the step of orally administering to a mammal, such as a human, a therapeutically effective amount of a new class of water-insoluble noncrosslinked amine polymers.

The water-insoluble noncrosslinked amine polymer comprises an amine-containing monomer or repeat unit which has one or more substituents bound to an amine nitrogen of the amine polymer. The substituent or substituents which are bound to the amine nitrogens of the amine polymer include a hydrophobic moiety and/or a quaternary amine-containing moiety.

27 Claims, 1 Drawing Sheet

U.S. PATENT DOCUMENTS

| | | |
|---|---|---|
| 3,383,281 | 5/1968 | Wolf et al. ................. 167/65 |
| 3,562,266 | 2/1971 | Minisci et al. . |
| 3,692,895 | 9/1972 | Nelson et al. ............. 424/78 |
| 3,780,171 | 12/1973 | Irmscher et al. .......... 424/79 |
| 3,787,474 | 1/1974 | Daniels et al. ........... 260/459 |
| 3,801,641 | 4/1974 | Payot et al. . |
| 3,803,237 | 4/1974 | Lednicer et al. ........ 260/584 R |
| 3,980,770 | 9/1976 | Ingelman et al. ......... 424/79 |
| 4,027,009 | 5/1977 | Grier et al. .............. 424/78 |
| 4,071,478 | 1/1978 | Shen et al. ............. 260/2 R |
| 4,098,726 | 7/1978 | Wagner et al. ......... 528/403 |
| 4,101,461 | 7/1978 | Strop et al. ............ 521/32 |
| 4,111,859 | 9/1978 | Strop et al. ............ 521/33 |
| 4,205,064 | 5/1980 | Wagner et al. ......... 424/78 |
| 4,217,429 | 8/1980 | Wagner et al. ......... 525/411 |
| 4,340,585 | 7/1982 | Borzatta et al. ......... 424/79 |
| 4,426,489 | 1/1984 | Wessling et al. ....... 524/815 |
| 4,540,760 | 9/1985 | Harada et al. .......... 526/211 |
| 4,557,930 | 12/1985 | Kihara et al. ........... 424/79 |
| 4,559,391 | 12/1985 | Ueda et al. ............. 525/366 |
| 4,605,701 | 8/1986 | Harada et al. .......... 525/107 |
| 4,680,360 | 7/1987 | Ueda et al. ............. 526/310 |
| 4,759,923 | 7/1988 | Buntin et al. .......... 424/440 |
| 5,055,197 | 10/1991 | Albright et al. ........ 210/638 |
| 5,142,019 | 8/1992 | Sundararaman et al. ..... 528/271 |
| 5,189,111 | 2/1993 | Danner ................ 525/328.2 |
| 5,236,701 | 8/1993 | St. Pierre et al. ....... 424/78 |
| 5,300,566 | 4/1994 | Pinschmidt, Jr. et al. ..... 525/60 |
| 5,374,422 | 12/1994 | St. Pierre et al. ..... 424/78.12 |
| 5,395,896 | 3/1995 | Moriya et al. ........... 525/60 |
| 5,414,068 | 5/1995 | Bliem et al. ............ 528/288 |
| 5,428,112 | 6/1995 | Ahlers et al. ......... 525/326.7 |
| 5,430,110 | 7/1995 | Ahlers et al. ......... 525/328.2 |
| 5,451,397 | 9/1995 | Albright et al. ....... 424/78.01 |
| 5,462,730 | 10/1995 | McTaggart et al. ..... 424/78.35 |
| 5,500,212 | 3/1996 | Bliem et al. .......... 424/78.12 |
| 5,618,530 | 4/1997 | Mandeville, III et al. ..... 424/78.12 |
| 5,703,188 | 12/1997 | Mandeville, III et al. ..... 526/290 |

FOREIGN PATENT DOCUMENTS

| | | |
|---|---|---|
| 0 373 852 A2 | 6/1990 | European Pat. Off. . |
| 0432995A1 | 6/1991 | European Pat. Off. . |
| 0 459 632 A1 | 12/1991 | European Pat. Off. . |
| 0 580 078 A1 | 1/1994 | European Pat. Off. . |
| 0 580 079 A1 | 1/1994 | European Pat. Off. . |
| 798488 | 7/1958 | United Kingdom . |
| 929391 | 6/1963 | United Kingdom . |
| 1567294 | 5/1980 | United Kingdom . |
| 2 090 605 | 7/1982 | United Kingdom . |
| WO91/18027 | 11/1991 | WIPO . |
| 92/10522 | 6/1992 | WIPO . |
| 94/04596 | 3/1994 | WIPO . |
| WO94/27620 | 12/1994 | WIPO . |
| WO 95/34585 | 12/1995 | WIPO . |
| WO 95/34588 | 12/1995 | WIPO . |
| 98/29107 | 9/1998 | WIPO . |

OTHER PUBLICATIONS

Dubin, P.L. and Davis, D.D., "Quasi–Elastic Light Scattering of Polyelectrolyte–Micelle Complexes," *Macromolecules* 17: 1294–1296 (1984).

Wang, G.–J. and Engberts, J., "Fluorescence probing of the formation of hydrophobic microdomains by cross–linked poly(alkylmethyldiallylammonium bromides) in aqueous solution," *Recl. Trav. Chim. Pays–Bas* 113:390–393 (1994).

Kunitake, T., et a., "Catalyses of Polymer Complexes. 4. Polysoap–Catalyzed Decarboxylation of 6–Nitrobenzisoxazole–3–carboxylate Anion. Importance of the Hydrophobic Environment in Activation of the Anion," *J. Org. Chem* 42(2) : 306–312 (1977).

Wang, G.–J. and Engberts, J., "Study of the Conformational State of Non–Cross–Linked and Cross–Linked Poly(alkylmethyldiallylammonium Chlorides) in Aqueous Solution by Fluorescence Probing," *Gazzetta Chimica Italiana*, 125: 393–397 (1995).

Kuron, G.W., et al., "The Bile Acid Binding and Hypocholesterolemic Action of Two Water–Soluble Polymers," *Atherosclerosis*, 37 353–360 (1980).

Harada, S. and Arai, K., "The Cyclo–copolymerization of Diallyl Compounds and Sulfur Dioxide," *Die Makromolekulare Chemie* 107: 64–93 (1967).

Wang, G.–J. and Engberts, J., "Induction of Aggregate Formation of Cationic Polysoaps and Surfactants by Low Concentrations of Additives in Aqueous Solution," *Langmuir*, 10(8): 2583–2587 (1994).

Wang, G.–J. and Engberts, J., "Synthesis of Hydrophobically and Electrostatically Modified Polyacrylamides and Their Catalytic Effects on the Unimolecular Decarboxylation of 6–Nitrobenzisoxazole–3–carboxylate Anion," *Langmuir*, 11(10): 3856–3861 (1995).

Wang, G.–J. and Engberts, J., "Synthesis and Catalytic Properties of Non–Cross–Linked and Cross–Linked Poly-(alkylmethyldiallylammonium bromides) Having Decyl, Octyl, and Hexyl Side Chains," *J. Org. Chem*, 60: 4030–4038 (1995).

Kevelam, J., et al., "Polymer–Surfactant Interactions Studied by Titration Microcalorimetry: Influence of Polymer Hydrophobicity, Electrostatic Forces, and Surfactant Aggregational State," *Langmuir*, 12(20): 4709–4717 (1996).

Wang, G.–J. and Engberts, J., "Synthesis and Catalytic Properties of Cross–Linked Hydrophobically Associating Poly(alkylmethyldiallylammonium bromides)," *J. Org. Chem.*, 59(15): 4076–4081 (1994).

Yang, Y.J. and Engberts, J., "Synthesis and Catalytic Properties of Hydrophobically Modified Poly(alkylmethyldiallylammonium bromides)," *J. Org. Chem.*, 56: 4300–4304 (1991).

Negi, Y., et al., "Cyclopolymerization of Diallylamine Derivatives in Dimethyl Sulfoxide," *J. of Polymer Science: Part A–1*, 5: 1951–1965 (1967).

Hodgkin, H. et al., "Use of $^{13}$C–NMR in the Study of Reactions on Crosslinked Resins," Published by John Wiley & Sons, *J. of Polymer Science: Polymer Chemistry Edition*, 19(5): 1239–1249 (1981).

Yeh, F., et al., "Nanoscale Supramolecular Structures in the Gels of Poly(Diallyldimethylammonium Chloride) Interacting with Sodium Dodecyl Sulfate," *J. Am. Chem. Soc.*, 118(28): 6615–6618 (1996).

Boothe, J.E., et al., "Some Homo–and Copolymerization Studies of dimethyldiallylammonium Chloride," *J. Macromol. Sci.–Chem.*, A4(6): 1419–1430 (1970).

United States Ser. No. 08/777,408, filed on Dec. 30, 1996, "Poly (diallylamine)—Based Bile Acid Sequestrant" by Stephen Randall Holmes–Farley, Pradeep K. Dhal and John S. Petersen.

WATER-INSOLUBLE NONCROSSLINKED BILE ACID SEQUESTRANTS

RELATED APPLICATIONS

This application is a Continuation-in-Part of U.S. application Ser. No. 08/659,264, filed Jun. 6, 1996, now U.S. Pat. No. 5,900,475, which is a Continuation-In-Part of application Ser. No. 08/469,659, filed Jun. 6, 1995, now U.S. Pat. No. 5,618,530 which is a Continuation-In-Part of applications having Ser. No. 08/258,431, filed Jun. 10, 1994 and Ser. No. 08/332,096, filed Oct. 31, 1994, both now abandoned. This application is also a Continuation-in-Part of application Ser. No. 08/482,969, filed Jun. 7, 1995 now U.S. Pat. No. 5,703,188 which is a Continuation-in-Part of application Ser. No. 08/258,477, filed Jun. 10, 1994 now U.S. Pat. No. 5,624,963, which is a Continuation-In-Part of application Ser. No. 08/071,564, filed Jun. 2, 1993, now abandoned. This application is also a Continuation-In-Part of application Ser. No. 08/779,779, filed Jan. 1, 1997 now U.S. Pat. No. 5,919,832 which is a divisional of Ser. No. 08/471,769 filed Jun. 6, 1995, now U.S. Pat. No. 5,607,669 which is a Continuation-in-Part of applications having Ser. No. 08/258,431, filed Jun. 10, 1994, now abandoned and Ser. No. 08/332,096, now abandoned. This application is also a Continuation-in-Part of application Ser. No. 08/461,298, filed Jun. 5, 1995 now U.S. Pat. No. 5,693,675 and Ser. No. 08/910,692 filed on Aug. 13, 1997, now abandoned, which is a divisional of Ser. No. 08/460,980, filed Jun. 5, 1995, now U.S. Pat. No. 5,679,717. Applications having Ser. No. 08/461,298 now U.S. Pat. No. 5,693,675 and Ser. No. 08/460,980 now U.S. Pat. No. 5,679,717 are Continuation-In-Part applications of Ser. No. 08/258,431, filed Jun. 10, 1994 now abandoned. The teachings of all of the above listed documents are incorporated herein by reference in their entirety.

BACKGROUND OF THE INVENTION

Biologically, cholesterol is eliminated from the body by conversion to bile acids and excretion as neutral steroids. Bile acids are synthesized from cholesterol in the liver and enter the bile as glycine and taurine conjugates. They are released in salt form with bile during digestion and act as detergents to solubilize and consequently aid in digestion of dietary fats. Following digestion, bile acid salts are mostly reabsorbed in the ileum, complexed with proteins and returned to the liver through hepatic portal veins. The small amount of bile acid salts which is not reabsorbed by active transport is excreted via the distal ileum and large intestine, which represents a major route for the elimination of cholesterol from the body.

Therefore, reabsorption of bile acids, which can be present as the corresponding salts or conjugates, from the intestine conserves lipoprotein cholesterol in the bloodstream. As such, reducing reabsorption of bile acids within the intestinal tract can lower levels of bile acid circulating in the enterohepatic system, thereby promoting replacement of bile acids through synthesis from cholesterol in the liver. The result is a lowering of circulating blood cholesterol levels.

One method of reducing the amount of bile acids that is reabsorbed is oral administration of compounds that sequester the bile acids within the intestinal tract and cannot themselves be absorbed. The sequestered bile acids consequently are excreted.

SUMMARY OF THE INVENTION

The present invention relates to a method for sequestering bile acids in a patient and to particular polymers for use in the method. The method comprises the step of orally administering to a mammal, such as a human, a therapeutically effective amount of a new class of water-insoluble noncrosslinked amine polymers.

The water-insoluble noncrosslinked amine polymer comprises an amine-containing monomer or repeat unit which has one or more substituents bound to an amine nitrogen of the amine polymer. The substituent or substituents which are bound to the amine nitrogens of the amine polymer include a hydrophobic moiety and/or a quaternary amine-containing moiety.

The amine polymer can be a homopolymer or a copolymer. The additional monomer of the copolymer can be an amine-containing or nonamine-containing monomer. The water-insoluble noncrosslinked amine polymer of the invention can also exist as a pharmaceutically acceptable salt.

In a particular embodiment, the method includes orally administering to a mammal, such as a human, a therapeutic amount of a water-insoluble noncrosslinked amine polymer comprising an amine-containing monomer or repeat unit having a first substituent, bound to an amine of the amine polymer, that includes a hydrophobic moiety and a second substituent bound to an amine of the amine polymer, the second substituent including a quaternary amine-containing moiety. It is to be understood that one or more of the terminal substituents of the quaternary amine-containing moiety can be a hydrophobic alkyl group.

In another embodiment, the method includes orally administering to a mammal, such as a human, a therapeutic amount of a water-insoluble noncrosslinked amine polymer comprising an amine-containing monomer or repeat unit having a substituent bound to an amine of the amine polymer that includes a hydrophobic moiety.

In a further embodiment, the method includes orally administering to a mammal, such as a human, a therapeutic amount of a water-insoluble noncrosslinked amine polymer comprising an amine-containing monomer or repeat unit having a substituent bound to an amine of the amine polymer that includes a quaternary amine-containing moiety having at least one terminal hydrophobic alkyl group.

This invention has many advantages. For example, the water-insoluble noncrosslinked amine polymers of the invention are less likely to be absorbed by the patient, thereby limiting any unwanted side effects associated with absorption. In addition, the water-insoluble noncrosslinked amine polymers of the invention are more efficacious than soluble polymers because they are held in a preformed matrix into which bile acids can be readily absorbed. These polymers, however, are not as rigidly fixed as those which are covalently crosslinked and, therefore, are more flexible and able to adjust position in order to accommodate binding of bile acids. Further, the polymers of the invention, due to their water insolubility, are able to be isolated and purified using water-based techniques which often are less expensive, less time consuming, and typically generate less waste. Also, since crosslinking is not required to render the bile acid sequestrants of the invention water insoluble, the process is faster and cheaper.

DETAILED DESCRIPTION OF THE INVENTION

Figure 1:
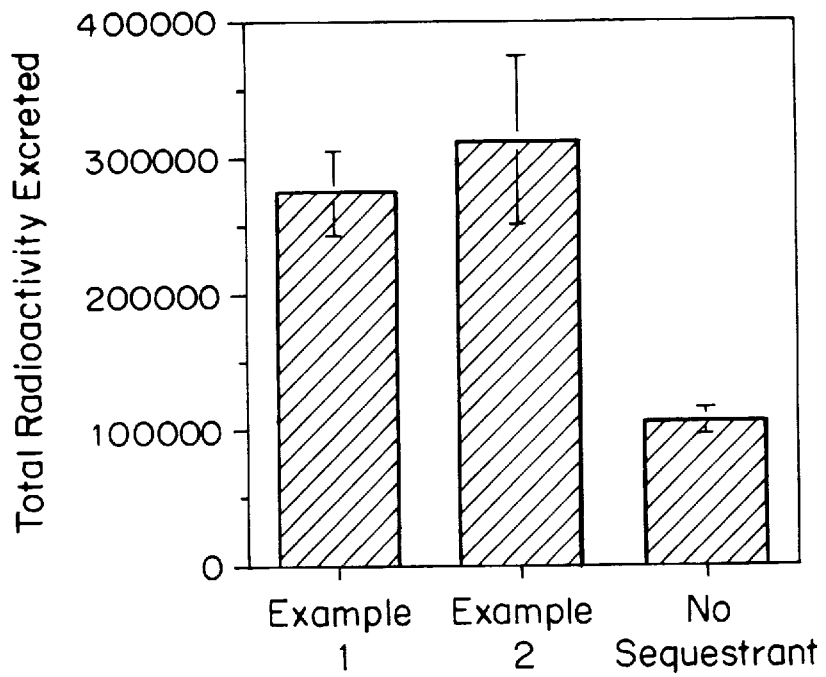
FIG. 1 is a bar graph showing the results of an in vivo test used to evaluate the efficacy of compounds as bile acid sequestrants. The compounds employed in the test were a noncrosslinked water-insoluble amine polymer and the corresponding crosslinked amine polymer.

The features and other details of the invention will now be more particularly described and pointed out below as well as in the claims. It will be understood that the particular embodiments of the invention are shown by way of illustration and not as limitations of the invention. The principle features of this invention can be employed in various embodiments without departing from the scope of the invention.

The water-insoluble noncrosslinked amine polymers of the invention comprise an amine-containing monomer or repeat unit which has one or more substituents bound to an amine nitrogen of the amine polymer. The substituent or substituents which are bound to the amine nitrogens of the amine polymer can include a hydrophobic moiety and/or a quaternary amine-containing moiety. In specific embodiments one or more of the terminal substituents of the quaternary amine-containing moiety can be a hydrophobic alkyl group.

"Water-insoluble," as that term is employed herein, means that the solubility of the polymer is less than or equal to about 5 grams per liter of water.

In a particular embodiment, the water-insoluble noncrosslinked amine polymer comprises an amine-containing monomer or repeat unit having distinct first and second substituents bound to an amine nitrogen of the polymer. The first substituent is bound to an amine of the amine polymer and includes a hydrophobic moiety. The second substituent is bound to an amine of the amine polymer and includes a quaternary amine-containing moiety having at least one terminal hydrophobic alkyl group. It is to be understood that the first and second substituents can be bound to the same amine and/or different amines of the amine polymer.

In another embodiment, the water-insoluble noncrosslinked amine polymer comprises an amine-containing monomer or repeat unit having one or more substituents bound to an amine nitrogen of the amine polymer which include a hydrophobic moiety.

In a further embodiment the water-insoluble noncrosslinked amine polymer comprises an amine-containing monomer or repeat unit having one or more substituents bound to an amine nitrogen of the amine polymer which includes a quaternary amine-containing moiety having at least one terminal hydrophobic alkyl group.

As used herein, the term "amine-containing monomer" includes any monomer or repeat unit which contains an amine. Suitable amine-containing monomers or repeat units can include those which upon polymerization yield an acyclic polymer. These amine-containing monomers or repeat units include, but are not limited to, for example, vinylamine, allylamine, and ethyleneimine.

Certain amine-containing monomers suitable for use in the invention can be achieved by chemically altering a particular repeat unit by reactions such as hydrolysis, nucleophilic substitution and reduction to yield a repeat unit or monomer having an amine. For example, polymerization of acrylamide gives poly(acrylamide) which can be reduced using reduction reactions well known in the art to give poly(allylamine). In accordance with the invention, the poly(allylamine) can then be further modified by substituting a portion of the amine nitrogens with at least one substituent which includes a hydrophobic moiety and/or a quaternary amine-containing moiety having at least one terminal hydrophobic alkyl group.

A "hydrophobic moiety," as the term is used herein, is a moiety which, as a separate entity, is more soluble in octanol than water. For example, the octyl group ($C_8H_{17}$) is hydrophobic because its parent alkane, octane, has greater solubility in octanol than in water. The hydrophobic moiety can be a saturated or unsaturated, substituted or unsubstituted hydrocarbon group. Such groups include substituted and unsubstituted, normal, branched or cyclic alkyl groups having at least six carbon atoms, substituted or unsubstituted arylalkyl or heteroarylalkyl groups and substituted or unsubstituted aryl or heteroaryl groups. In one embodiment, the hydrophobic moiety includes an alkyl group of between about eight and twelve carbons. Preferably, the hydrophobic moiety includes an alkyl group of about ten carbons. Specific examples of suitable hydrophobic moieties include the following alkyl groups n-hexyl, n-heptyl, n-octyl, n-nonyl, n-decyl, n-undecyl, n-dodecyl, n-tetradecyl, n-octadecyl, and combinations thereof. Other examples of suitable hydrophobic moieties include haloalkyl groups of at least six carbons (e.g., 1-halodecane), hydroxyalkyl groups of at least six carbons (e.g., 1-undecanol) and aralkyl groups (e.g., benzyl).

Suitable substituents which include a quaternary amine-containing moiety include an alkyl trialkylammonium also referred to as an ammonioalkyl group. The term "ammonioalkyl," as used herein, refers to an alkyl group which is substituted by a nitrogen bearing three additional substituents. It is to be understood that one or more of the three additional substituents can be a hydrophobic alkyl group. Thus, the nitrogen atom is an ammonium nitrogen which bears an alkylene substituent, which links the ammonium nitrogen atom to the nitrogen atom of the amine-containing monomer or repeat unit, and has three additional terminal alkyl substituents having from about one to about twenty-four carbons. One or more of the three terminal substituents can be a hydrophobic alkyl group having from six to about twenty-four carbons. A "terminal substituent," as the term is employed herein, is any one of the three substituents on the quaternary amine nitrogen which is not the carbon chain between the amine on the polymer backbone and the amine of the quaternary ammonium center.

In one embodiment, the terminal substituents are each independently a normal or branched, substituted or unsubstituted alkyl group having from one to about twenty-four carbons. In another embodiment, at least one of the three terminal substituents can be a hydrophobic alkyl group having from six to about twenty-four carbons, the remainder having from one to about twenty-four carbons. In yet another embodiment, at least two of the three terminal substituents can be hydrophobic alkyl groups having from six to about twenty-four carbons, the remainder having from one to about twenty-four carbons. In a further embodiment, all three of the terminal substituents can be hydrophobic alkyl groups having from six to about twenty-four carbons.

Suitable ammonioalkyl groups are of the general formula:

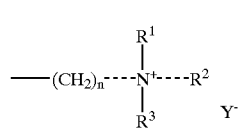
(I)

wherein, $R^1$, $R^2$ and $R^3$ represent an alkyl group, wherein each R, independently, is a normal or branched, substituted or unsubstituted alkyl group having a carbon atom chain length of between about one to about twenty-four carbon atoms, n is an integer having a value of three or more, and Y is a negatively charged counterion. In a particular embodiment, $R^1$, $R^2$, and $R^3$ are all methyl groups, and n is an integer between about 3 and about 12 (e.g., 3, 4, 5, 6, 7, 8, 9, 10, 11, or 12).

The alkyl group, which provides the alkylene linking group between the amine of the amine-containing monomer or repeat unit and the ammonium nitrogen of the alkyl trialkylammonium group, is three or more carbon atoms in length. Examples of preferred alkylene linking groups are propyl, butyl, pentyl, hexyl, octyl, and decyl groups. Examples of suitable quaternary amine-containing moieties include, but are not limited to:
4-(trimethylammonio)butyl;
6-(trimethylammonio)hexyl;
8-(trimethylammonio)octyl;
10-(trimethylammonio)decyl;
12-(trimethylammonio)dodecyl;
and combinations thereof. A particularly preferred amine-containing moiety is a 6-(trimethylammonio)hexyl group. It is to be understood that although the alkyl group of the alkyl trialkylammonium group, which links the ammonium center to the amine of the polymer composition, may in some instances be at least six carbon atoms in length, this is not considered a hydrophobic substituent, as defined herein.

In a specific embodiment, at least one of $R^1$, $R^2$ and $R^3$ is a hydrophobic alkyl group having from six to about twenty-four carbons which can be normal or branched, substituted or unsubstituted, and the remaining terminal substituents are each, independently, a normal or branched, substituted or unsubstituted alkyl group having a carbon atom chain length of between about one to about twenty-four carbon atoms, n is an integer having a value of three or more, for example, between 3 and 12 as earlier described, and Y is a negatively charged counterion. In another embodiment, at least two of the three terminal substituents can be hydrophobic alkyl groups having from six to about twenty-four carbon atoms, the remainder having from one to about twenty-four carbons. In a further embodiment, all three of the terminal substituents can be hydrophobic alkyl groups having from six to about twenty-four carbons.

A "hydrophobic alkyl group," as that term is employed herein, is an alkyl group having from six to about twenty-four carbons and which is terminated in a hydrophobic moiety. The hydrophobic alkyl group can be, for example, a normal or branched, substituted or unsubstituted alkyl group having from six to about twenty-four carbons. The hydrophobic alkyl group does not include the alkylene between the nitrogen of the amine polymer and the nitrogen of the quaternary ammonium center.

Examples of preferred hydrophobic alkyl groups include, but are not limited to, hexyl, heptyl, octyl, nonyl, decyl, undecyl, dodecyl, docosyl, and tetradecyl groups. The hydrophobic alkyl groups can contain ethers, thioethers, halogens, and combinations thereof.

Particular examples of quaternary amine-containing moieties, which provide a substituent including a quaternary amine-containing moiety with at least one terminal hydrophobic alkyl group, include, but are not limited to:
4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
3-(dimethyldecylammonio)hexyl;
6-(decyldimethylammonio)hexyl;
3-(tridecylammonio)propyl;
3-(docosyldimethylammonio)propyl;
6-(docosyldimethylammonio)hexyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
4-(dioctylmethylammonio)butyl;
6-(octyldimethylammonio)hexyl;
12-(decyldimethylammonio)dodecyl;
3-(dimethylundecylammnio)propyl; and
3-(tetradecyldimethylammonio)propyl.

The negatively charged counterion is a conjugate base of a pharmaceutically acceptable acid. Examples of suitable counterions include $Cl^-$, $Br^-$, $CH_3OSO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, and a nucleotide.

The substituents are typically bound to the amines of the amine-containing monomer or repeat unit, by reaction with an alkylating agent which provides the desired substituent. When the hydrophobic moiety and the quaternary amine-containing moiety are both present in the water-insoluble noncrosslinked amine polymer of the invention, reaction with at least two alkylating agents is therefore necessary. However, when the hydrophobic moiety or the quaternary amine-containing moiety is present separately, reaction with one alkylating agent is sufficient to provide the water-insoluble noncrosslinked amine polymers of the invention.

The water-insoluble noncrosslinked amine polymers of the invention can be formed by reacting a noncrosslinked polymer with a suitable alkylating agent or by polymerizing an alkylated monomer.

An "alkylating agent," as that term is employed herein, means a reactant that, when reacted with an amine-containing monomer or polymer characterized by an amine-containing repeat unit of the invention, causes a substituent having a hydrophobic moiety and/or a substituent having a quaternary amine-containing moiety having at least one terminal hydrophobic alkyl group, as earlier described, to be covalently bound to one or more of the amine nitrogen atoms of the monomer or polymer repeat unit.

Suitable alkylating agents are compounds comprising an alkyl group or alkyl derivative, having at least six carbon atoms, or an ammonioalkyl group, which is bonded to a leaving group such as a halo (e.g., chloro, bromo or iodo), tosylate, mesylate, or epoxy group.

In one embodiment, the amine polymer is alkylated with a substituent which includes a hydrophobic moiety. Examples of suitable alkylating agents which provide a hydrophobic moiety include alkyl halides having at least six carbon atoms, such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include a dihaloalkane that includes an alkyl group of at least six carbons (e.g., a 1,10-dihalodecane); a hydroxyalkyl halide having at least six carbon atoms (e.g., an 11-halo-1-undecanol); and an aralkyl halide (e.g., a benzyl halide). Preferred halogens of the alkyl halides are bromine and chlorine.

In another embodiment, the amine polymer is alkylated with a substituent which includes a quaternary amine-containing moiety. Examples of suitable alkylating agents which provide a quaternary amine-containing moiety have the general formula:

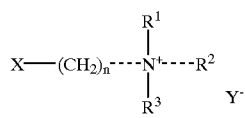

wherein $R^1$, $R^2$, and $R^3$ represent an alkyl group and each R independently is a normal or branched, substituted, or unsubstituted alkyl group having a carbon atom chain length of between about one to about twenty-four carbon atoms, n is an integer having a value of three or more, X is a leaving group, and Y is a negatively charged counterion.

In a specific embodiment, $R^1$, $R^2$ and $R^3$ represent an alkyl group, wherein at least one of $R^1$, $R^2$ and $R^3$ is a hydrophobic alkyl group having from six to about twenty-four carbons which can be normal or branched, substituted or unsubstituted and the remaining terminal substituents are each, independently, a normal or branched, substituted or unsubstituted alkyl group having a carbon atom chain length of between about one to about twenty-four carbon atoms, n is an integer having a value of three or more, X is a leaving group, and Y is a negatively-charged counterion.

Particular examples of quaternary ammonium compounds suitable as alkylating agents which provide a quaternary amine-containing moiety having at least one terminal hydrophobic alkyl group include, but are not limited to, the following:
(4-bromobutyl)dioctylmethylammonium bromide;
(3-bromopropyl)dodecyldimethylammonium bromide;
(3-chloropropyl)dodecyldimethylammonium bromide;
(3-chloropropyl)decyldimethylammonium bromide;
(5-tosylpentyl)dodecyldimethylammonium bromide;
(6-bromohexyl)dimethyldecylammonium bromide
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-bromopropyl)octyldimethylammonium bromide;
(3-iodobutyl)dioctylmethylammonium bromide;
(2,3-epoxy propyl)decyldimethylammonium bromide; and
(3-bromohexyl)docosyldimethyammonium bromide.

Particularly preferred quaternary amine alkylating agents are (6-bromohexyl)dimethyldecylammonium bromide and (3-chloropropyl)dodecyldimethylammonium bromide- Chloride salts, such as (3-chloropropyl) dodecyldimethylammonium chloride and (6-bromohexyl) dimethyldecylammonium chloride, are also preferred embodiments.

Examples of other suitable alkyl trialkyl ammonium alkylating agents include, but are not limited to, the following alkyl halide trimethylammonium salts:

(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonioum salt;
(10-halodecyl)trimethylammonium salt;
(11-haloundecyl)trimethylammonium salt;
(12-halododecyl)trimethylammonium salt;
and combinations thereof.

In another embodiment, the water-insoluble non-crosslinked amine polymer is alkylated with two alkylating agents. The first provides a substituent including a hydrophobic moiety, as described above, and the second provides a substituent which includes a quaternary amine-containing moiety as described above.

Alkylation is accomplished by combining the amine-containing monomer or the polymer comprising an amine-containing monomer or repeat unit with one or more alkylating agents, simultaneously or sequentially in any order. The total amount of the alkylating agent or agents combined is generally sufficient to render the resulting alkylated polymer water-insoluble. Typically, the amount of alkylating agent employed is sufficient to cause reaction with between about 40 and 100 percent of the amine nitrogens available. Preferably the range is between about 50 and 100 percent. Examples of suitable solvents include, but are not limited to, methanol, ethanol, isopropanol, acetonitrile, water, and mixtures thereof. Preferred solvents are methanol, ethanol, isopropanol, water, and mixtures thereof.

Examples of suitable methods by which amine polymers can be formed are shown below:

1. One method involves polymerization of an amine monomer to form a homopolymer. Examples of this method include polymerization of allylamine, ethyleneimine, vinylamine, 1,2-diaminoethene, aminopropylacrylate, or p-aminomethylstyrene, to form their respective homopolymers.

2. Another method involves copolymerizing an amine monomer with one or more additional monomers. These additional monomers can include amine monomers, such as those listed above, and non-amine monomers, such as acrylamide, styrene, vinyl alcohol, or vinyl chloride. Examples of copolymers can include copoly(allylamine/acrylamide) or copoly(vinylamine/allylamine).

3. Still another method involves polymerization of a non-amine monomer to form a homopolymer that is subsequently chemically modified to form an amine polymer. Examples of this method include polymerization of vinyl formamide, vinyl acetamide, vinyl chloride, vinyl bromide, allyl chloride, allyl bromide, acrylamide, or acrylonitrile, to form their respective homopolymers. Each homopolymer would then be chemically altered to form an amine polymer using such reactions as hydrolysis, nucleophilic substitution, or reduction. The first four homopolymers listed above would then become poly(vinylamine) and the last four would become poly(allylamine). It is to be understood that not all of the initial non-amine monomer need be chemically altered, resulting in an amine polymer that contains some of the initial non-amine monomers in a non-amine state.

4. A fourth method involves copolymerizing a non-amine monomer with one or more additional monomers. These additional monomers could include amine monomers, such as those listed in the first method, and non-amine monomers, such as those listed in the third method. The resulting copolymer would then be chemically altered to form an amine polymer as in the third method. Examples would include copolymerization of acrylamide and styrene, followed by reduction to form copoly(allylamine/styrene), copolymerization of acrylonitrile and vinyl formamide, followed by reduction and hydrolysis, to form copoly (allylamine/vinylamine), and copolymerization of acrylonitrile and allylamine, followed by reduction, to form poly (allylamine). It is to be understood that not all of the initial non-amine monomer be chemically altered, resulting in an amine polymer that contains some of the initial non-amine monomers in a non-amine state.

As such, the water-insoluble noncrosslinked amine polymers of the invention include homopolymers and copolymers, as described above. The water-insoluble non-crosslinked amine polymers of the invention can exist in the form of a pharmaceutically acceptable salt. By "salt" is meant that the nitrogen group in the repeat unit is protonated or alkylated to create a positively charged nitrogen atom associated with a negatively charged counterion.

The water-insoluble noncrosslinked amine polymers may therefore have fixed positive charges, or may have the capability of becoming charged upon ingestion at physiological pH. In the latter case, the charged ions also pick up negatively charged counterions upon ingestion that can be exchanged with bile salts. In the case of polymer having fixed positive charges, however, the reaction product may be provided with one or more exchangeable counterions. Examples of suitable counterions include $Cl^-$, $Br^-$, $CH_3OSO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, or a nucleotide. The counterions may be the same as, or different from, each other. For example, the water-insoluble noncrosslinked amine polymer may contain two different types of counterions, both of which are exchanged for the bile salts being removed. More than one reaction product, each having different counterions associated with the fixed charges, may be administered as well.

Each of these amine polymers typically has a molecular weight greater than about 2,000. Examples of resulting suitable amine polymers include poly(vinylamine), poly (allylamine), and poly(ethyleneimine)polymers. A preferred amine polymer is poly(allylamine).

Preferred embodiments of the amine polymer formed by this method include a water-insoluble noncrosslinked poly (allylamine) polymer having a substituent which includes a quaternary amine-containing moiety having at least one terminal hydrophobic alkyl group. The alkylene is three carbons in length, the terminal hydrophobic alkyl group can be a heptyl, octyl, nonyl, decyl, undecyl or dodecyl group, and the remaining terminal substituents can be methyl groups. In particularly preferred embodiments, the alkylene chain is three or four carbon atoms in length, the terminal hydrophobic alkyl group is dodecyl, and the remaining terminal substituents are methyl groups.

Methods of use of the water-insoluble noncrosslinked amine polymers of the invention include their oral administration to a mammal in a therapeutic amount to bind bile acid salts, reduce blood cholesterol, treat atherosclerosis, treat hypercholesterolemia, and reduce plasma lipid content of the mammal. Generally, a therapeutic amount of the amine polymers is an amount in a range of from about 1 mg/kg/day to about 10 g/kg/day, preferably between about 1 mg/kg/day to about 200 mg/kg/day.

In one embodiment, the method of the invention is a method for binding bile salts in a mammal, comprising the step of orally administering to the mammal a therapeutic amount of a water-insoluble noncrosslinked amine polymer of the invention.

In another embodiment, the method of the invention is a method for reducing blood cholesterol in a mammal, comprising the step of orally administering to the mammal a therapeutic amount of a water-insoluble noncrosslinked amine polymer of the present invention. In still another embodiment, the invention includes a method for treating atherosclerosis in a mammal, comprising the step of administering to the mammal a therapeutic amount of a water-insoluble noncrosslinked amine polymer of the invention.

In a further embodiment, the method of the invention is a method of treating hypercholesterolemia in a mammal, comprising the step of administering to the mammal a therapeutic amount of a water-insoluble noncrosslinked amine polymer of the invention.

Another embodiment of the invention is a method for reducing plasma lipid content of a mammal, comprising the step of orally administering to the mammal a water-insoluble noncrosslinked polymer of the invention.

As used herein, the terms "therapeutically effective amount" and "therapeutic amount" are synonymous. The terms refer to an amount which is sufficient to bind bile acid salts, reduce blood cholesterol, treat atherosclerosis, and treat hypercholesterolemia. The mammal can be a human.

The water-insoluble noncrosslinked amine polymers of this invention are particularly suitable for binding bile acids in mammals by oral administration of the polymer. The water-insoluble noncrosslinked amine polymer of the invention can be subsequently treated or combined with other materials to form a composition for oral administration of the amine polymer. Such compositions include combination with other known cholesterol lowering agents, such as lovastatin and niacin.

The present pharmaceutical compositions are generally prepared by known procedures using well known and readily available ingredients. In making the compositions of the present invention, the amine polymer can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, and talc.

The invention will now be further and specifically described by the following examples. All parts and percentages are by weight unless otherwise specified.

EXEMPLIFICATIONS

EXAMPLE 1

Aqueous polyallylamine hydrochloride (25.6 g of 50% solution; Nitto Boseki) was dissolved in water (100 mL) in a 1 L, 3-necked flask equipped with a condenser, thermometer, and a mechanical stirrer. Aqueous sodium hydroxide (7.6 g of 50% solution) was added. (3-Chloropropyl)dimethyldodecylammonium bromide (140 g) was added along with water (200 mL). The mixture was heated with stirring to 100° C., at which time it was clear and homogeneous. After 5 minutes the solution started to become cloudy, and significant precipitate was evident after 30 minutes. Aqueous sodium hydroxide (30 g of 50% solution) was added in 10 portions (3 g each) at 45 minute intervals. The heating and stirring were continued at 100° C. for a total heating period of 24 hours.

The reaction was then cooled to room temperature, and water (500 mL) was added. The mixture was stirred for 10 minutes, and the solid was collected by filtration. The solids were rinsed on the funnel with water (1 L) and suspended in aqueous sodium chloride (1.6 L of 2 M NaCl). The mixture was stirred for 30 minutes, and the solid again collected by filtration. The solids were rinsed twice more with aqueous sodium chloride as above and then rinsed with water until conductivity reached 0.01< mS/cm. The pH was then adjusted with concentrated HCl from 8.5 to 2.5, with sufficient HCl added to maintain the pH at 2.5 after one hour of stirring. The solids were again collected by filtration and the wet solution (129.1 g) was dried in a forced air oven at 60° C. for 18 hours to yield 72.7 g of white solid. The solid was then ground on a rotary mill and was passed through a mesh sieve.

The solid product is readily soluble in methanol (>10 g/L), demonstrating that it is not covalently crosslinked. It is insoluble in water (<0.1 g/L). The product was analyzed and found to contain 59.98% C, 11.38% H, 6.09% N, 14.98% Cl, and 0.5% Br.

EXAMPLE 2

Crosslinked Version of Example 1

To a five gallon vessel was added poly(allylamine) hydrochloride (1 kg) obtained from Nitto Boseki and water (4 L). The mixture was stirred to dissolve the hydrochloride, and the pH was adjusted by adding solid NaOH (284 grams). The resulting solution was cooled to room temperature, after which epichlorohydrin crosslinking agent (25 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about three minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield 3% crosslinked poly (allylamine) as a granular, brittle, white solid.

To a 2 L round-bottomed flask were added crosslinked poly(allylamine) (25 g; 3% crosslinked; ground to –10 mesh), (3-chloropropyl)dimethyldodecylammonium bromide (280 g), water (750 mL), and aqueous sodium hydroxide (6.1 g of 50% NaOH). The mixture was heated to 100° C. with stirring. Upon reaching 100° C., aqueous sodium hydroxide was added in nine portions at 45 minute intervals (each portion=6.1 g of 50% solution). Heating was continued for a total of 24 hours at 100° C., and the mixture was allowed to cool to 50° C. Hydrochloric acid (50 mL of concentrated HCl) was added with stirring, and the solid was collected by filtration.

The solids were rinsed in a funnel with methanol (1.5 L) and then resuspended in methanol (2 L). After stirring for 230 minutes, the solid was again collected by filtration and resuspended in aqueous sodium chloride (3.3 L of 2 M NaCl). The mixture was stirred for 30 minutes, and the solid collected by filtration. The solids were rinsed twice more with aqueous sodium chloride as above and then rinsed with water until the conductivity reached 0.34 ms/cm. The pH was then adjusted with concentrated HCl from 4.2 to 2.2, with sufficient HCl added to maintain the pH at 2.2 after 1 hour of stirring. The solids were collected by filtration, and the wet solid (178.6 g) was dried in a forced air oven at 60° C. for 18 hours to yield 111.1 g of white solid. The solid was then ground on a rotary mill and was passed through a 140 mesh sieve.

The solid product was insoluble in methanol and water (<0.1 g/L). The product was analyzed and found to contain 61.74% C. 11.53% H, 6.64% N, 16.08% Cl, and <0.1% Br.

EXAMPLE 3

Soluble, Non-Crosslinked Gel

Aqueous poly(allylamine hydrochloride (11.6 g of 50% solution; 5.8 g dry equivalent) was added to a 250 mL round-bottomed flask equipped with a thermometer, air condenser, heating mantle, and a mechanical stirrer. Aqueous sodium hydroxide (3.2 g of 50% solution; 1.6 g dry equivalent) was added, and the mixture stirred briefly. To this solution was added (6-bromohexyl)trimethylammonium bromide (8.1 g), 1-bromodecane (5.5 g), and methanol (127 mL). The flask was purged with $N_2$ for 15 minutes and then heated to 65° C. Upon reaching 65° C., aqueous sodium hydroxide (1.1 g of 50% solution) was added and the stirring continued at 65° C. for 2 hours. Aqueous sodium hydroxide (1.1 g of 50% solution) was added and the stirring continued at 65° C. for an additional 2 hours. Aqueous sodium hydroxide (1.2 g of 50% solution) was added and the stirring continued at 65° C. for an additional 2 hours. Aqueous sodium hydroxide (1.1 g of 50% solution) was added and the stirring continued at 65° C. for an additional 12 hours.

The mixture was allowed to cool to room temperature (~2 hours) and then sealed into dialysis tubing (SpectraPor MWCO 3500). The tubing was stirred in methanol (7 L) for 18 hours. The methanol was then replaced with fresh methanol and the stirring continued 8 hours. The tubing was then placed into aqueous sodium chloride (7 L of 2 M NaCl) and stirred for 24 hours. The NaCl solution was replaced with fresh solution, and the stirring was continued for an additional 24 hours. The tubing was then transferred to deionized water (7 L) and stirred for 1 hour. The water was replaced and the tubing stirred for 90 minutes. The water was changed again, and the tubing was stirred for 18 hours. The solution was stirred for 5 hours, and the water changed again. The tubing was stirred for an additional 2 hours, and the contents were removed.

Hydrochloric acid (concentrated, 4.0 mL) was added, and the solution was transferred to a separatory funnel. Hydrophobic impurities were extracted with diethylether (100 mL) and the aqueous phase was dried in a forced air oven at 60° C. for 24 hours to yield 6.8 g of a brittle solid. The solid was ground and passed through a 140 mesh sieve. The product was soluble in water (>30 g/L). The product was analyzed and found to contain 52.04% C, 10.39% H, 8.56% N, 22.14% Cl, and <0.1% Br.

EXAMPLE 4

Crosslinked Version of Example 3

To a five gallon vessel was added poly(allylamine) hydrochloride (1 kg) obtained from Nitto Boseki and water (4 L).

The mixture was stirred to dissolve the hydrochloride, and the pH was adjusted by adding solid NaOH (284 grams). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for one hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield 3% crosslinked poly (allylamine) as a granular, brittle, white solid.

To a large flask was added crosslinked poly(allylamine) (200 g; 6% crosslinked ground to -10 mesh), (6-bromohexyl)trimethylammonium bromide (322.1 g), 1-bromodecane (221.1 g), and methanol (5.3 L). The mixture was heated to 65° C. with stirring under nitrogen. Upon reaching 65° C., aqueous sodium hydroxide (45.1 g of 50% solution) was added and the stirring continued at 65° C. for 2 hours. Aqueous sodium hydroxide (45.1 g of 50% solution) was added and the stirring continued at 65° C. for an additional 12 hours. The mixture was then allowed to cool to room temperature (~4 hours). Concentrated HCl (160 mL) was added and the mixture stirred for 30 minutes.

The solid product was filtered off and rinsed on the funnel with methanol (8 L). The solid was resuspended in methanol (3 L), stirred for 30 minutes, and collected by filtration, from the following fluids:

1. 8 L 2M NaCl (aqueous)
2. 8 L 2M NaFl (aqueous)
3. 8 L 2M NaCl (aqueous)
4. Wash with water until the conductivity=0.8 mS/cm.

The solid was then dried in a 60° C. forced air drying oven to yield 458 g of an off-white solid. The solid was then ground and passed through a 140 mesh sieve. The product was analyzed and found to contain 54.74% C, 11.04% H, 8.40% N, 20.30% Cl, and 0.33% Br.

IN VIVO TESTING OF EXAMPLES 1–4

The sequestrants made in the examples above were tested in vivo in hamsters. The animals were injected peritoneally with a solution of $^{14}C$ labeled bile acids (Cholic:Chenodeoxycholic) that exist in gallbladder bile. They enter the gallbladder and are incorporated into the animals' endogenous pool of bile. The animals were then fed a diet containing drug (0.30% by weight) for 36 hours, and the feces were collected over the final 29 hours. Fecal samples were then processed and counted for radioactivity. More potent bile acid sequestrants result in the removal of larger amounts of bile, and consequently showed higher radioactivity. The control sample was nonzero due to the natural loss of some bile acids in the feces of normal animals.

FIG. 1 shows the total amount of radioactivity that was excreted from animals fed the sequestrants made in the examples. The error bars represent the 90% confidence intervals on the true sample means.

From FIG. 1, it is apparent that the potencies of Example 1 (noncrosslinked, insoluble sequestrant), and Example 2 (crosslinked, insoluble sequestrant) are comparable (within a 90% confidence interval). This result provides evidence that a noncovalently crosslinked bile acid sequestrant that is insoluble in water has comparable efficacy to one that contains covalent crosslinks. In other words, the lack of covalent crosslinks does not detract from the potency of this drug, probably because it is already insoluble in water.

Figure 2:
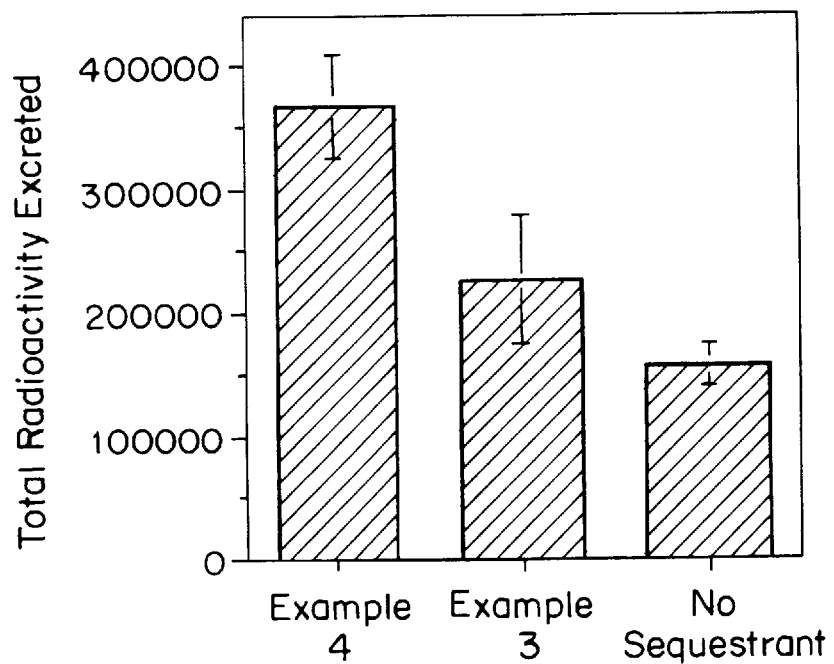
FIG. 2 is a bar graph showing the results of an in vivo test used to evaluate the efficacy of compounds as bile acid sequestrants. The compounds employed in the test were a water soluble noncrosslinked amine polymer and the corresponding water-insoluble crosslinked amine polymer.

FIG. 2 shows a similar in vivo comparison between Examples 3 and 4. From FIG. 2, it is apparent that Example 3 (soluble, noncrosslinked sequestrant) is less effective than Example 4 (the polymer of Example 3, but with covalent crosslinking). This result provides evidence that fully water-soluble bile acid sequestrants will not be as effective as those with a similar structure that are insoluble. In this case, the covalent crosslinking prevented Example 4 from dissolving, and thus made it a much more potent bile acid sequestrant. In other words, the lack of covalent crosslinks does detract from potency when the sequestrant is water soluble.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain, using no more than routine experimentation, many equivalents to the specific embodiments of the invention described specifically herein. Such equivalents are intended to be encompassed in the scope of the claims.

What is claimed is:

1. A method for binding bile salts in a mammal, comprising the step of orally administering to the mammal a therapeutic amount of a water-insoluble noncrosslinked amine polymer having a substituent bound to an amine nitrogen of the amine polymer, the substituent including a quaternary amine-containing moiety.

2. The method of claim 1 wherein said quaternary amine-containing moiety has the chemical formula:

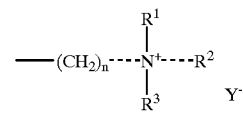

$R^1$, $R^2$ and $R^3$ represent an alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

3. The method of claim 2 wherein one of $R^1$, $R^2$, and $R^3$ is a dodecyl group, the remaining groups are methyl groups and n is three.

4. The method of claim 2 wherein one of $R^1$, $R^2$, and $R^3$ is a dodecyl group, the remaining groups are methyl groups and n is four.

5. The method of claim 2 wherein one of $R^1$, $R^2$, and $R^3$ is a dodecyl group, the remaining groups are methyl groups and n is six.

6. A method for binding bile salts in a mammal, comprising the step of orally administering to the mammal a therapeutic amount of a water-insoluble noncrosslinked amine polymer having a first substituent, bound to an amine nitrogen of the amine polymer, that includes a hydrophobic moiety and a second substituent bound to an amine nitrogen of the amine polymer, the second substituent including a quaternary amine-containing moiety.

7. The method of claim 6 wherein said hydrophobic moiety is a decyl group.

8. The method of claim 6 wherein said quaternary amine-containing moiety has the chemical formula:

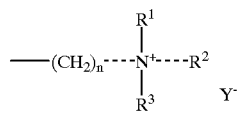

$R^1$, $R^2$ and $R^3$ represent an alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

9. A method for binding bile salts in a mammal, comprising the step of orally administering to the mammal a therapeutic amount of a water-insoluble noncrosslinked amine polymer having a substituent bound to an amine nitrogen of the amine polymer, the substituent including a hydrophobic moiety.

10. A method for reducing blood cholesterol in a mammal, comprising the step of orally administering to the mammal a therapeutic amount of a water-insoluble noncrosslinked amine polymer having a substituent bound to an amine nitrogen of the amine polymer, the substituent including a quaternary amine-containing moiety.

11. The method of claim 10 wherein said quaternary amine-containing moiety has the chemical formula:

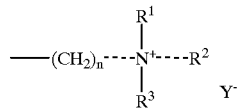

$R^1$, $R^2$ and $R^3$ represent an alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

12. The method of claim 11 wherein one of $R^1$, $R^2$, and $R^3$ is a dodecyl group, the remaining groups are methyl groups and n is three.

13. The method of claim 11 wherein one of $R^1$, $R^2$, and $R^3$ is a dodecyl group, the remaining groups are methyl groups and n is four.

14. The method of claim 11 wherein one of $R^1$, $R^2$, and $R^3$ is a dodecycl group, the remaining groups are methyl groups and n is six.

15. A method for reducing blood cholesterol in a mammal, comprising the step of orally administering to the mammal a therapeutic amount of a water-insoluble noncrosslinked amine polymer having a first substituent, bound to an amine nitrogen of the amine polymer, that includes a hydrophobic moiety and a second substituent bound to an amine of the amine polymer, the second substituent including a quaternary amine-containing moiety.

16. The method of claim 15 wherein said hydrophobic moiety is a decyl group.

17. The method of claim 15 wherein said quaternary amine-containing moiety has the chemical formula:

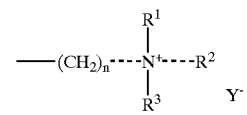

$R^1$, $R^2$, and $R^3$ represent an alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

18. A method for reducing blood cholesterol in a mammal, comprising the step of orally administering to the mammal a therapeutic amount of a water-insoluble noncrosslinked amine polymer having a substituent bound to an amine nitrogen of the amine polymer, the substituent including a hydrophobic moiety.

19. A water-insoluble noncrosslinked amine polymer having a substituent bound to an amine nitrogen of the amine polymer, the substituent including a quaternary amine-containing moiety.

20. The polymer of claim 19 wherein said quaternary amine-containing moiety has the chemical formula:

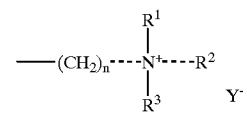

$R^1$, $R^2$ and $R^3$ represent an alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

21. The polymer of claim 20 wherein one of $R^1$, $R^2$, and $R^3$ is a dodecyl group, the remaining groups are methyl groups and n is three.

22. The polymer of claim 20 wherein one of $R^1$, $R^2$, and $R^3$ is a dodecyl group, the remaining groups are methyl groups and n is four.

23. The polymer of claim 20 wherein one of $R^1$, $R^2$, and $R^3$ is a dodecyl group, the remaining groups are methyl groups and n is six.

24. A water-insoluble noncrosslinked amine polymer having a first substituent, bound to an amine nitrogen of the amine polymer, that includes a hydrophobic moiety and a second substituent bound to an amine nitrogen of the amine polymer, the second substituent including a quaternary amine-containing moiety.

25. The polymer of claim 24 wherein said hydrophobic moiety is a decyl group.

26. The polymer of claim 24 wherein said quaternary amine-containing moiety has the chemical formula:

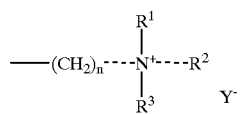

$R^1$, $R^2$ and $R^3$ represent alkyl group, wherein each R, independently, is a normal or branched, substituted or unsubstituted alkyl group having a carbon atom chain length of between about one to about twenty-four carbon atoms;

n is an integer having a value of three or more; and

Y is a negatively-charged counterion.

27. A water-insoluble noncrosslinked amine polymer having a substituent bound to an amine nitrogen of the amine polymer, the substituent including a hydrophobic moiety.

* * * * *